(12) United States Patent
Ahmad et al.

(10) Patent No.: US 8,333,977 B2
(45) Date of Patent: Dec. 18, 2012

(54) INACTIVATED STAPHYLOCOCCAL WHOLE-CELL VACCINE

(75) Inventors: Afshan Ahmad, Birmingham (GB); Bruce Robert Gordon Skinner, Birmingham (GB)

(73) Assignee: Vaccine Research International PLC, Birmingham (GB)

( * ) Notice: Subject to any disclaimer, the term of this patent is extended or adjusted under 35 U.S.C. 154(b) by 286 days.

(21) Appl. No.: 12/669,453

(22) PCT Filed: Jul. 23, 2007

(86) PCT No.: PCT/GB2007/002792
§ 371 (c)(1), (2), (4) Date: Jan. 15, 2010

(87) PCT Pub. No.: WO2009/013443
PCT Pub. Date: Jan. 29, 2009

(65) Prior Publication Data
US 2010/0189748 A1 Jul. 29, 2010

(51) Int. Cl.
*A61K 39/085* (2006.01)
(52) U.S. Cl. .................. 424/243.1; 435/243; 435/252.1; 424/234.1
(58) Field of Classification Search .......... None
See application file for complete search history.

(56) References Cited

FOREIGN PATENT DOCUMENTS

| WO | WO 90/11087 | 10/1990 |
| WO | WO 00/12131 | 3/2000 |
| WO | WO 01/70267 | 9/2001 |

OTHER PUBLICATIONS

Ahmed et al., "Sequential Release of Antigens from Chloroform-Treated *Staphylococcus epidermidis*: Application Towards a Possible Vaccine," *Journal of Applied Bacteriology*, 69(5): 676-685, (1990).
Ahmed, "Vaccine Against Staphylococal Infections," Retrieved from the Internet: URL:http://www.congress.is/vaccine/lectures/Staphylococal%2Ovaccines-Ahmed.pdf>, (Sep. 22, 2006).
International Search report and Written Opinion for PCT Application No. PCT/GB2007/002792, 15 pp., (May 14, 2008).
Skinner et al., "Staphylococal Vaccines: Present Status amd Future Prospects," *Zentralblatt Fuer Bakteriologie Supplement*, 26(0): 537-550, (1994).
*Vaccine Research International PLC*, Quarterly Report & Management Accounts, Sep. 30, 2006, Retrieved from the Internet: URL:http://www.vri.org.uk/QReportSept06.pdf> [Retrieved on Apr. 10, 2008], (Oct. 31, 2006).
*Vaccine Research International PLC*, Quarterly Report & Management Accounts, Dec. 31, 2006, Retrieved from the Internet: URL:http://www.vri.org.uk/QLYREPTDEC06.pdf> [Retrieved on Apr. 10, 2008], (Oct. 31, 2006).

*Primary Examiner* — Jennifer Graser
(74) *Attorney, Agent, or Firm* — Klarquist Sparkman, LLP

(57) ABSTRACT

A vaccine is disclosed that is protective against pathogenic bacterial species, typically staphylococcal species, and includes methods to prepare said vaccine and to culture pathogenic bacteria.

17 Claims, 13 Drawing Sheets

Figure 9

Table 1

| Vaccine Dose (mg) | A | B | C | D | E | F | G | H | Total |
|---|---|---|---|---|---|---|---|---|---|
| | \multicolumn{9}{c}{No. Events (Maximum Reported Grade; No. Events at Maximum Reported Grade)*} |
| Placebo | 1 (Mild; 1) | 2 (Mild; 2) | 1 (Mild; 1) | 0 | 2 (Mild; 2) | 0 | 0 | 0 | 6 |
| 0.15 | 22 (Mod.; 5) | 41 (Mod.; 1) | 1 (Mild; 1) | 0 | 50 (Mild; 50) | 2 (Mild; 2) | 0 | 1 (Mild; 1) | 117 |
| 0.36 | 42 (Mod.; 2) | 43 (Mod.; 1) | 2 (Mild; 2) | 1 (Mild; 1) | 45 (Mod.; 5) | 5 (Mild; 5) | 0 | 7 (Mild; 7) | 145 |
| .045 | 38 (Sev.; 2) | 51 (Sev.; 2) | 3 (Mild; 3) | 0 | 89 (Sev.; 2) | 15 (Mod.; 2) | 1 (Sev.; 1) | 3 (Mod.; 2) | 197 |

A = Erythema    C = Haemmorrhage    E = Pain    G = Swelling
B = Induration  D = Burning         F = Pruritis H = Warmth

Figure 10

Table 2

| Vaccine Dose (mg) | A | B | C | D | E | F | Total | No. Discontinuations |
|---|---|---|---|---|---|---|---|---|
| | | | No. Events (Maximum Reported Grade; No. Events at Maximum Reported Grade)* | | | | | |
| Placebo | 0 | 0 | 3 (Sev.; 1) | 0 | 0 | 3 (Mild; 3) | 23 | 0 |
| 0.15 | 2 (Mild; 2) | 0 | 3 (Mod.; 2) | 0 | 0 | 6 (Mild; 6) | 29 | 1 not vaccine-related |
| 0.36 | 0 | 0 | 1 (Mod.; 1) | 0 | 0 | 7 (Mod.; 2) | 19 | 1 not vaccine-related; 1 flu-like symptoms |
| .045 | 0 | 3 (Mod.; 1) | 4 (Mod.; 2) | 3 (Sev.; 1) | 3 (Sev.; 2) | 16 (Mod.; 8) | 63 | 1 severe injection site erythema |

A = Fatigue  
B = Feeling hot/cold  
C = Flu-like  
D = Malaise  
E = Vomiting  
F = Headache

Figure 11

Table 3

*Weak – 0-4 positive changes
**Strong – 5 or more positive changes

| Vaccine Dose (mg) | None | Weak* | Reaction | Strong** |
|---|---|---|---|---|
| Placebo | 7/12 | 5/12 | | 0/12 |
| 0.15 | 0/12 | 6/12 | | 6/12 |
| 0.36 | 0/12 | 2/12 | | 9/12 |
| 0.45 | 0/12 | 0/12 | | 12/12 |

Figure 12

Table 4

| Vaccine Dose | Number of Subjects/Total Number of Subjects |
|---|---|
| Placebo | 1/12 |
| 0.15mg Vaccine | 7/12 |
| 0.36mg Vaccine | 9/12 |
| 0.45mg Vaccine | 7/12 |

Figure 13

Table 5

(Secondary study objective – Non-GLP testing)
Serum from 32* volunteers taken 3 and 6 months after 4th vaccination – comparison with reactivity at 2 weeks following 4th (final) vaccination:

|  | Group 1 (0.15mg) | Group 2 (0.45mg) | Group 3 (0.36mg) |
|---|---|---|---|
| Vaccinated Subjects | | | |
| Above pre immune level at 3 and 6 months | 11/11 | 11/11 | 10/10** |
| Placebo | | | |
| No change in reactivity at 3 and 6 months | 4/4 | 4/4 | 4/4 |

\* Volunteers lost to follow up 007, 020, 036 and 044.
\*\* Volunteer 047 (Group 3) who did not have a sample at 6 months

INACTIVATED STAPHYLOCOCCAL WHOLE-CELL VACCINE

CROSS REFERENCE TO RELATED APPLICATIONS

This is the U.S. national stage of PCT Application No. PCT/GB2007/002792, filed Jul. 23, 2007, which was published in English under PCT Article 21(2).

The invention relates to a vaccine that is protective against pathogenic bacterial species, typically staphylococcal species, and including methods to prepare said vaccine and to culture pathogenic bacteria.

Vaccines protect against a wide variety of infectious diseases. Many vaccines are produced by inactivated or attenuated pathogens which are injected into a subject. The immunised subject responds by producing both a humoral (e.g. antibody) and cellular (e.g. cytolytic T cells) responses For example, some influenza vaccines are made by inactivating the virus by chemical treatment with formaldehyde, likewise the Salk polio vaccine comprises whole virus inactivated with propionolactone. For many pathogens chemical or heat inactivation while it may give rise to vaccine immunogens that confer protective immunity also gives rise to side effects such as fever and injection site reactions. In the case of bacteria, inactivated organisms tend to be so toxic that side effects have limited the application of such crude vaccine immunogens (e.g. the cellular pertussis vaccine) and therefore vaccine development has lagged behind drug-development. This is unfortunate as current antibiotic treatments are now prejudiced by the emergence of drug-resistant bacteria.

An example of a pathogenic organism which has developed resistance to antibiotics is *Staphylococcus aureus*. *S. aureus* is a bacterium whose normal habitat is the epithelial lining of the nose in about 20-40% of normal healthy people and is also commonly found on people's skin usually without causing harm. However, in certain circumstances, particularly when skin is damaged, this pathogen can cause infection. This is a particular problem in hospitals where patients may have surgical procedures and/or be taking immunosuppressive drugs. These patients are much more vulnerable to infection with *S. aureus* because of the treatment they have received. Resistant strains of *S. aureus* have arisen in recent years. Methicillin resistant strains are prevalent and many of these resistant strains are also resistant to several other antibiotics. Currently there is no effective vaccination procedure for *S. aureus*.

*S. aureus* is therefore a major human pathogen capable of causing a wide range of diseases some of which are life threatening diseases including septicaemia, endocarditis, arthritis and toxic shock. This ability is determined by the versatility of the organism and its arsenal of components involved in virulence. At the onset of infection, and as it progresses, the needs and environment of the organism changes and this is mirrored by a corresponding alteration in the virulence determinants which *S. aureus* produces. At the beginning of infection it is important for the pathogen to adhere to host tissues and so a large repertoire of cell surface associated attachment proteins are made. These include collagen-, fibrinogen- and fibronectin-binding proteins. The pathogen also has the ability to evade host defenses by the production of factors that reduce phagocytosis or interfere with the ability of the cells to be recognised by circulating antibodies. Often a focus of infection develops as an abscess and the number of organisms increases. *S. aureus* has the ability to monitor its own cell density by the production of a quorum sensing peptide. Accumulation of the peptide, associated with physiological changes brought about by the beginning of starvation of the cells, elicits a switch in virulence determinant production from adhesins to components involved in invasion and tissue penetration. These include a wide range of hemolysins, proteases and other degradative enzymes; (see also, Manual of Clinical Microbiology Fourth Edition. Editors Edwin H Lennette, Albert Balows, William J Hausler Jr, H Jean Shadomy; published by the Americal Society for Microbiology 1985).

We disclose the development of a chloroform-inactivated whole bacterial vaccine using a clinical isolate of *S. aureus* which is selected as being representative of a spectrum of *S. aureus* strains which were tested by a number of criteria. The antigenicity of the vaccine designated SA75 has been demonstrated by enzyme linked immunosorbent assay (ELISA) and western blotting with hyperimmune rabbit serum and the vaccine produced a dose related immune response in both male and female rabbits. Preliminary data from a placebo controlled double blind Phase I clinical trial of the vaccine in human male volunteers demonstrated that the vaccine was both safe and immunogenic. It also cross-reacts with many other pathogenic bacteria and therefore provides a vaccine that is protective to a wide range of bacterial pathogens. In addition we describe cell culture conditions that are substantially free of animal derived products and the use of these conditions in vaccine production.

According to an aspect of the invention there is provided a vaccine composition comprising an inactivated staphylococcal cell wherein said composition is prepared using a staphylococcal cell characterised in that said cell:

i) is a gram positive cocci;
ii) expresses at least the enzyme catalase;
iii) induces an immune response that produces antibodies that bind at least staphylococcal collagen-binding protein; and
iv) is resistant to the antibiotic penicillin.

The staphylococcal bacterial cell is characterised by a number of biological and biochemical features that include the expression of selected genes (e.g., urease and arginine dihydrolase); the sensitivity to a number of antibiotics and including the ability to metabolise carbohydrate sources, the reduction of nitrate and methyl carbinol In a preferred embodiment of the invention said staphylococcal cell also expresses the enzymes coagulase and/or Dnase.

In a further preferred embodiment of the invention said staphylococcal cell induces an immune response that produces antibodies that bind collagen binding protein.

In a further preferred embodiment of the invention said inactivated staphylococcal cell induces an immune response that produces antibodies that cross react with methicillin resistant, vancomycin resistant and vancomycin intermediate resistant staphylococcal species.

In a further preferred embodiment of the invention said staphylococcal cell is sensitive to the antibiotics cloxacillin, erythromycin, tetracycline and gentamicin.

In a preferred embodiment of the invention said staphylococcal cell is selected from the group consisting of: *S. epidermidis, S. aureus, S. hominis, S. haemolyticus, S. warneri, S. capitis, S. saccharolyticus, S. auricularis, S. simulans, S. saprophyticus, S. cohnii, S. xylosus, S. cohnii, S. warneri, S. hyicus, S. caprae, S. gallinarum, S. intermedius, S. hominis*.

In a further preferred embodiment of the invention said staphylococcal cell is *S. aureus* or *S. epidermidis*.

In a further preferred embodiment of the invention said staphylococcal cell is an antibiotic resistant staphylococcal cell.

In a preferred embodiment of the invention said antibiotic resistance staphylococcal cell is a methicillin resistant staphylococcal cell (MRSA).

In an alternative preferred embodiment of the invention said antibiotic resistance staphylococcal cell is a vancomycin resistant staphylococcal cell (VRSA).

In a further preferred embodiment of the invention said staphylococcal cell is a *Staphylococcus aureus* cell designated as P/DFO 75 (National Collection of Type Cultures (NCTC) deposited on 19 Jun. 2007; accession number 13408; Deposited under the Budapest Treaty on the International Recognition of the deposit of Micro-organisms as amended in 1980).

In a preferred embodiment of the invention said staphylococcal cell is provided at a protein concentration of not more than about 1 mg bacterial protein/ml.

In a preferred embodiment of the invention said staphylococcal cell is provided at a protein concentration of not more than about 0.45 mg bacterial protein/ml.

In a further preferred embodiment of the invention said staphylococcal cell is provided at a protein concentration of at least 0.0001 mg bacterial protein/ml In a further preferred embodiment of the invention said staphylococcal cell is provided at a protein concentration of at least 0.1 mg bacterial protein/ml In a further preferred embodiment of the invention said staphylococcal cell is provided at a protein concentration of between 0.0001-1 mg bacterial protein/ml.

In a further preferred embodiment of the invention said staphylococcal cell is provided at a protein concentration of between 0.1-0.45 mg bacterial protein/ml.

In a still further preferred embodiment of the invention said staphylococcal cell is provided at between 0.25-0.36 mg bacterial protein/ml.

In a further preferred embodiment of the invention said staphylococcal cell is provided at about 0.35 mg bacterial protein/ml.

In a preferred embodiment of the invention said vaccine composition comprises an adjuvant and/or excipient.

An adjuvant is a substance or procedure which augments specific immune responses to antigens by modulating the activity of immune cells. Examples of adjuvants include, by example only, agonistic antibodies to co-stimulatory molecules, Freunds adjuvant, muramyl dipeptides, liposomes. An adjuvant is therefore an immunomodulator.

The vaccine compositions of the invention can be administered by any conventional route, including injection, intranasal spray by inhalation of for example an aerosol or nasal drops, or by gradual infusion over time The administration may be, for example, intravenous, intraperitoneal, intramuscular, intracavity, subcutaneous, or transdermal. The vaccine compositions of the invention are administered in effective amounts. An "effective amount" is that amount of a vaccine composition that alone or together with further doses, produces the desired response. In the case of treating a particular bacterial disease the desired response is providing protection when challenged by an infective agent.

In a preferred embodiment of the invention said vaccine composition is adapted for administration as a nasal spray.

In a preferred embodiment of the invention said vaccine composition is provided in an inhaler and delivered as an aerosol.

According to a further aspect of the invention there is provided an inhaler comprising a vaccine composition according to the invention.

Such amounts of vaccine will depend, of course, on the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation.

It is generally preferred that a maximum dose of the individual components or combinations thereof be used sufficient to provoke immunity; that is, the highest safe dose according to sound medical judgment. It will be understood by those of ordinary skill in the art, however, that a patient may insist upon a lower dose or tolerable dose for medical reasons, psychological reasons or for virtually any other reasons.

The vaccine compositions used in the foregoing methods preferably are sterile and contain an effective amount of staphylococci for producing the desired response in a unit of weight or volume suitable for administration to a patient. The doses of vaccine administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of vaccine are formulated and administered in doses between 0.1 mg and 0.45 mg and preferably between 0.15 mg and 0.4 mg, according to any standard procedure in the art. Other protocols for the administration of the vaccine compositions will be known to one of ordinary skill in the art, in which the dose amount, schedule of injections, sites of injections, mode of administration and the like vary from the foregoing. Administration of the vaccine compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the vaccine compositions of the invention are applied in therapeutically acceptable amounts and in therapeutically acceptable compositions. The term "therapeutically acceptable" means a non-toxic material that does not interfere with the effectiveness of the biological activity of the active ingredients. Such preparations may routinely contain salts, buffering agents, preservatives, compatible carriers, and optionally other anti-bacterial agents. The vaccine compositions may contain suitable buffering agents, including: acetic acid in a salt; citric acid in a salt; boric acid in a salt; and phosphoric acid in a salt.

The vaccine compositions also may contain, optionally, suitable preservatives, such as: benzalkonium chloride; chlorobutanol; parabens and thiomerosal Vaccine compositions suitable for parenteral administration conveniently comprise a sterile aqueous or non-aqueous preparation of vaccine, which is preferably isotonic with the blood of the recipient. This vaccine may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for subcutaneous, intravenous, intramuscular, etc. administrations can be found in Remington's Pharmaceutical Sciences, Mack Publishing Co., Easton, Pa.

In a preferred embodiment of the invention there is provided a vaccine composition according to the invention that includes at least one additional anti-bacterial agent.

In a preferred embodiment of the invention said agent is a second different vaccine and/or immunogenic agent (for example a bacterial polypeptide and/or polysaccharide antigen).

According to a further aspect of the invention there is provided a staphylococcal cell characterised in that said cell:
i) is a gram positive cocci;
ii) expresses at least the enzyme catalase;
iii) induces an immune response that produces antibodies that bind at least staphylococcal collagen-binding protein;
iv) is resistant to the antibiotic penicillin;
for use in the manufacture of a vaccine composition for the vaccination of an animal subject with respect to a bacterial infection wherein said infection is not caused by a staphylococcal bacterial cell.

In a preferred embodiment of the invention said bacterial infection is caused by at least one bacterial cell selected from the group consisting of: *Enterococcus faecalis; Mycobacterium tuberculsis; Streptococcus* group B; *Streptococcus pneumoniae; Helicobacter pylori; Neisseria gonorrhoea; Streptococcus* group A; *Borrelia burgdorferi; Coccidiodes immitis; Histoplasma sapsulatum; Klebsiella edwardii; Neisseria meningitidis* type B; *Proteus mirabilis; Shigella flexneri; Escherichia coli; Haemophilus influenzae, Chalmydia trachomatis, Chlamydia pneumoniae, Chlamydia psittaci, Francisella tularensis, Pseudomonas aeruginos, Bacillus anthracis, Clostridium botulinum, Yersinia pestis, Burkholderia mallei* or *B pseudomallei.*

According to a further aspect of the invention there is provided a staphylococcal cell characterised in that said cell:
i) is a gram positive cocci;
ii) expresses at least the enzyme catalase;
iii) induces an immune response that produces antibodies that bind at least staphylococcal collagen-binding protein;
iv) is resistant to the antibiotic penicillin;
for use in the manufacture of a vaccine composition for the vaccination of an animal subject with respect to a yeast infection.

In a preferred embodiment of the invention said yeast infection is caused by a pathogenic yeast species, for example *Candida albicans* or *Saccharomyces cerevisiae.*

In a preferred embodiment of the invention said yeast infection is associated with an immune suppressed state; for example an immune suppressed state as a consequence of an HIV infection or as a result of the administration of immunosuppressive drugs.

In a preferred embodiment of the invention said animal subject is human.

According to a further aspect of the invention there is provided a method to vaccinate an animal against a bacterial infection comprising administering an effective amount of the vaccine composition according to the invention.

In a preferred method of the invention said animal is a human.

In a preferred method of the invention said bacterial infection is caused by a bacterial pathogen selected from the group consisting of: *Enterococcus faecalis; Mycobacterium tuberculsis; Streptococcus* group B; *Streptococcus pneumoniae; Helicobacter pylori; Neisseria gonorrhoea; Streptococcus* group A; *Borrelia burgdorferi; Coccidiodes immitis; Histoplasma sapsulatum; Klebsiella edwardii; Neisseria meningitidis* type B; *Proteus mirabilis; Shigella flexneri; Escherichia coli; Haemophilus influenzae, Chalmydia trachomatis, Chlamydia pneumoniae, Chlamydia psittaci, Francisella tularensis, Pseudomonas aeruginos, Bacillus anthracis, Clostridium botulinum, Yersinia pestis, Burkholderia mallei* or *B pseudomallei.*

In a preferred method of the invention said bacterial infection is caused by a bacterial cell selected from the group consisting of: *S. epidermidis, S. aureus, S. hominis, S. haemolyticus, S. warneri, S. capitis, S. saccharolyticus, S. auricularis, S. simulans, S. saprophyticus, S. cohnii, S. xylosus, S. cohnii, S. warneri, S. hyicus, S. caprae, S. gallinarum, S. intermedius, S. hominis.*

In a further preferred method of the invention said bacterial species is *S. aureus* or *S. epidermidis.*

In a further preferred method of the invention said bacterial infection is caused by an antibiotic resistant bacterial cell; preferably a staphylococcal bacterial cell.

In a preferred method of the invention said antibiotic resistance staphylococcal cell is a methicillin resistant staphylococcal species (MRSA).

In an alternative preferred method of the invention said antibiotic resistance staphylococcal cell is a vancomycin resistant staphylococcal cell (VRSA).

A preferred route of administration is intradermal, subcutaneous, intramuscular or intranasal (e.g. as an aerosol); however the vaccination method is not restricted to a particular mode of administration.

In a preferred method of the invention said bacterial infection results in a disease associated with a staphylococcal infection.

A staphylococcal associated disorder may include, for example, tuberculosis; bacteria-associated food poisoning; blood infections; peritonitis; endocarditis; osteomyelitis; sepsis; skin disorders, meningitis; pneumonia; stomach ulcers; gonorrhoea; strep throat; streptococcal-associated toxic shock; necrotizing fasciitis; impetigo; histoplasmosis; Lyme disease; gastro-enteritis; dysentery; shigellosis; and arthritis.

In an alternative preferred method of the invention said animal is a live stock animal.

In a preferred method of the invention said live stock animal is vaccinated against bacterial mastitis caused by gram positive cocci; preferably staphylococcal and/or streptococcal bacterial cells.

In a preferred method of the invention said bacterial mastitis is caused by *Staphylococcus aureus* and/or *Streptococcus agalactiae.*

In a preferred method of the invention said life stock animal is a caprine animal (e.g. sheep, goat).

In a preferred method of the invention said life stock animal is a bovine animal (e.g. a cow).

Staphylococcal mastitis is a serious condition that affects live stock and can result in considerable expense with respect to controlling the disease through administration of antibiotics and in terms of lost milk yield. The vaccine according to the invention provides cost effective control of bacterial, in particular staphylococcal mastitis.

According to a further aspect of the invention there is provided a method for preparing a hybridoma cell-line producing monoclonal antibodies that bind staphylococcal bacterial polypeptides comprising the steps of:

i) vaccinating an immunocompetent mammal with a vaccine composition according to the invention;
ii) fusing lymphocytes of the vaccinated immunocompetent mammal with myeloma cells to form hybridoma cells;
iii) screening monoclonal antibodies produced by the hybridoma cells of step (ii) for binding activity with respect to staphylococcal bacterial polypeptides;
iii) cloning the hybridoma cells and culturing the cells to proliferate and to secrete said monoclonal antibody; and
iv) recovering the monoclonal antibody from the culture supernatant.

Preferably, said immunocompetent mammal is a mouse. Alternatively, said immunocompetent mammal is a rat.

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

According to an aspect of the invention there is provided a hybridoma cell line formed by the method according to the invention.

According to a yet further aspect of the invention there is provided a monoclonal antibody produced by the hybridoma cell-line according to the invention.

In a preferred embodiment of the invention said monoclonal antibody is an opsonic antibody.

Phagocytosis is mediated by macrophages and polymorphic leukocytes and involves the ingestion and digestion of micro-organisms, damaged or dead cells, cell debris, insoluble particles and activated clotting factors. Opsonins are agents which facilitate the phagocytosis of the above foreign bodies. Opsonic antibodies are therefore antibodies which provide the same function. Examples of opsonins are the Fc portion of an antibody or compliment C3.

In a further preferred embodiment of the invention said monoclonal antibody or preferably opsonic antibody is chimeric or humanized by recombinant techniques to combine the complimentarity determining regions of said antibody with both the constant (C) regions and the framework regions from the variable (V) regions of a human antibody.

Chimeric antibodies are recombinant antibodies in which all of the V-regions of a mouse or rat antibody are combined with human antibody C-regions. Humanised antibodies are recombinant hybrid antibodies which fuse the complimentarity determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen. Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody.

In a further preferred embodiment of the invention there is provided an active binding fragment of said monoclonal antibody.

Various fragments of antibodies are known in the art, i.e., Fab, $Fab_2$, $F(ab')_2$, Fv, Fc, Fd, scFvs, etc. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A $Fab_2$ fragment comprises two joined Fab fragments. When these two fragments are joined by the immunoglobulin hinge region, a $F(ab')_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* or Janeway et al. *Immunobiology* (cited above). Molecular biology now allows direct synthesis (via expression in cells or chemically) of these fragments, as well as synthesis of combinations thereof. A fragment of an antibody can also have bispecific function as described above.

In a preferred embodiment of the invention there is provided human sera obtained by vaccination of a human subject with a vaccine composition according to the invention.

In a preferred embodiment of the invention there is provided a human antibody obtained by vaccination of a human subject with a vaccine composition according to the invention.

In a preferred embodiment of the invention said human antibody is an isotype selected from the group consisting of: IgA, IgM, IgD, IgE and IgG.

According to a further aspect of the invention there is provide the use of human sera obtained by vaccination with a vaccine composition according to the invention in the manufacture of a medicament for the treatment of a bacterial infection.

In a preferred embodiment of the invention said bacterial infection is a staphylococcal infection.

According to a further aspect of the invention there is provide the use of a human antibody obtained by vaccination with a vaccine composition according to the invention in the manufacture of a medicament for the treatment of a bacterial infection.

In a preferred embodiment of the invention said bacterial infection is a staphylococcal infection.

According to a further aspect of the invention there is provided a method to prepare a vaccine to a bacterial pathogen comprising the steps of:
i) forming a cell culture preparation comprising at least one bacterial pathogen and nutrient broth comprising plant derived products;

ii) culturing said cell culture preparation; and
iii) contacting said cell culture preparation with an agent that inactivates said bacterial pathogen.

In a preferred method of the invention said bacterial pathogen is selected from the group consisting of: *Staphylococcus aureus; Staphylococcus epidermidis; Enterococcus faecalis; Mycobacterium tuberculsis; Streptococcus* group B; *Streptococcus pneumoniae; Helicobacter pylori; Neisseria gonorrhoea; Streptococcus* group A; *Borrelia burgdorferi; Coccidiodes immitis; Histoplasma sapsulatum; Klebsiella edwardii; Neisseria meningitidis* type B; *Proteus mirabilis; Shigella flexneri; Escherichia coli; Haemophilus influenzae, Chalmydia trachomatis, Chlamydia pneumoniae, Chlamydia psittaci, Francisella tularensis, Pseudomonas aeruginos, Bacillus anthracis, Clostridium botulinum, Yersinia pestis, Burkholderia mallei* or *B pseudomallei*.

In a preferred method of the invention said bacterial pathogen is selected from the group consisting of: *S. epidermidis, S. aureus, S. hominis, S. haemolyticus, S. warneri, S. capitis, S. saccharolyticus, S. auricularis, S. simulans, S. saprophyticus, S. cohnii, S. xylosus, S. cohnii, S. warneri, S. hyicus, S. caprae, S. gallinarum, S. intermedius, S. hominis*.

In a preferred method of the invention said bacterial pathogen is *S. aureus* or *S. epidermidis*.

In an alternative preferred method of the invention said bacterial pathogen is selected from the group consisting of: *Streptococcus pneumoniae, Pseudomonas aeruginosa* or *Escherichia coli*.

In a further preferred method of the invention said plant derived product is vegetable peptone. Preferably said vegetable peptone includes pea flour and/or tryptone soya.

In a further preferred method of the invention said bacterial pathogen is inactivated with chloroform.

In a yet further preferred method of the invention said bacterial pathogen is isolated from said cell culture preparation and freeze dried.

According to a further aspect of the invention there is provided a process for the production of a vaccine comprising the steps of:
i) forming a preparation comprising a staphylococcal bacterial cell;
ii) contacting the preparation with an agent that inactivates the staphylococcal bacterial cell;
iii) isolating the inactivated staphylococcal bacterial cell;
iv) shearing said preparation to disaggregate the inactivated bacteria; and optionally
v) freeze drying said inactivated staphylococcal bacterial cell.

In a preferred method of the invention said staphylococcal cell is selected from the group consisting of: *S. epidermidis, S. aureus, S. hominis, S. haemolyticus, S. warneri, S. capitis, S. saccharolyticus, S. auricularis, S. simulans, S. saprophyticus, S. cohnii, S. xylosus, S. cohnii, S. warneri, S. hyicus, S. caprae, S. gallinarum, S. intermedius, S. hominis*.

In a preferred method of the invention said staphylococcal bacterial cell is *S. aureus* or *S. epidermidis*.

In a further preferred method of the invention said agent is chloroform.

In a preferred method of the invention shear force is provided by a dounce homogenizer.

According to a further aspect of the invention there is provided a *Staphylococcus aureus* cell deposited with the National Collection of Type Cultures (HPA Centre for Infections, 61 Collindale Avenue, London, NW9 5HT, England) in accordance with the Budapest Treaty under accession number 13408.

According to a yet further aspect of the invention there is provided a bacterial cell culture comprising a *Staphylococcus aureus* cell as deposited under accession number 13408.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures:

FIG. 9 is Table 1, which summarizes local effects of vaccine administered to subjects;

FIG. 10 is Table 2, which summarizes systemic effects of vaccine administered to subjects;

FIG. 11 is Table 3, which summarizes immune reactivity of sera from vaccinated and placebo subjects on western blotting;

FIG. 12 is Table 4, which illustrates the presence of antibodies to collagen-binding protein in vaccinated and placebo subjects FIG. 13 is Table 5, which illustrates the longevity of the immune response in vaccinated subjects.

Materials and Methods

Cell Culture and Vaccine Preparation

Figure 1:
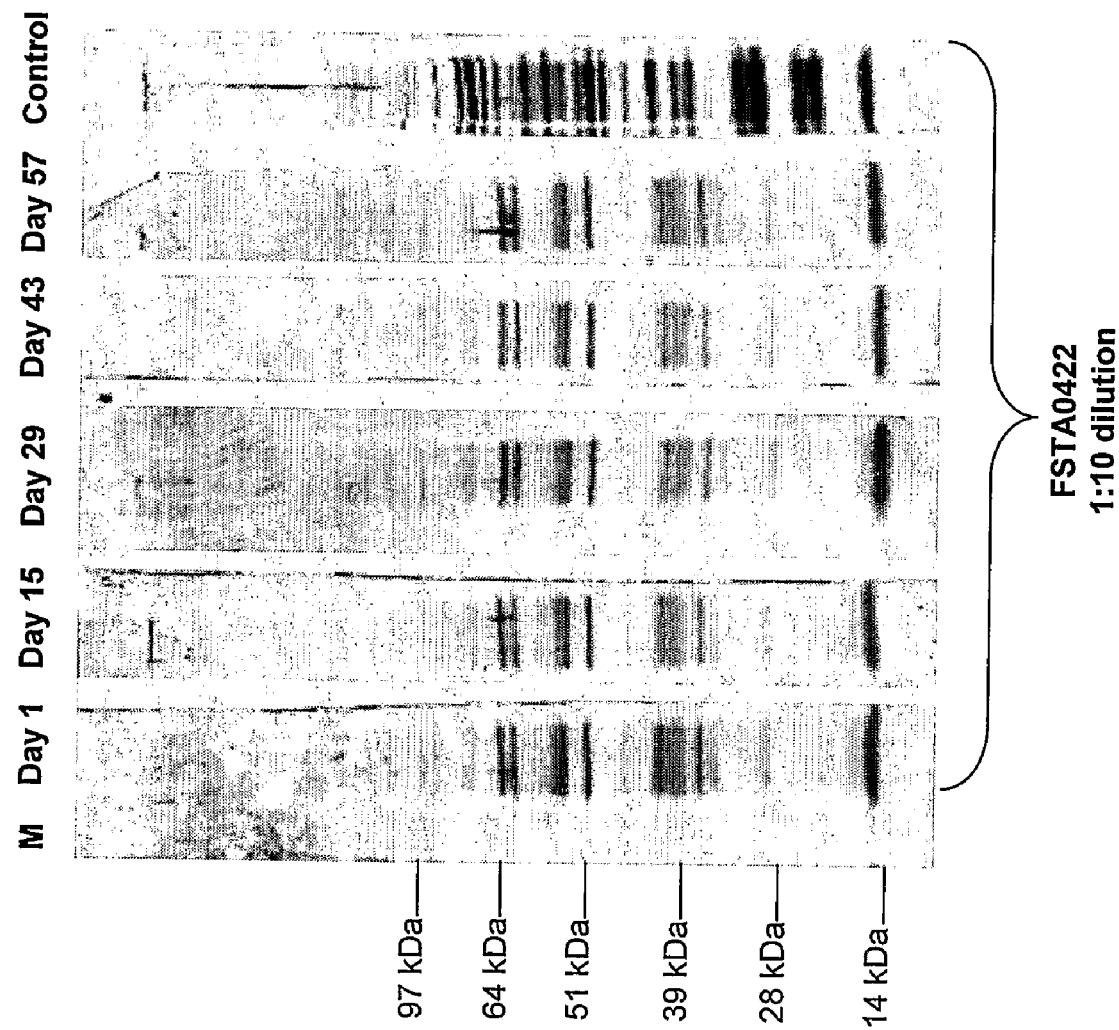
FIG. 1 illustrates the immune response of placebo subject on western blotting. Day 1—before vaccination; day 15—after one vaccination; day 29—after two vaccinations, day 43 after three vaccinations and day 57—after four vaccinations.
Figure 2:
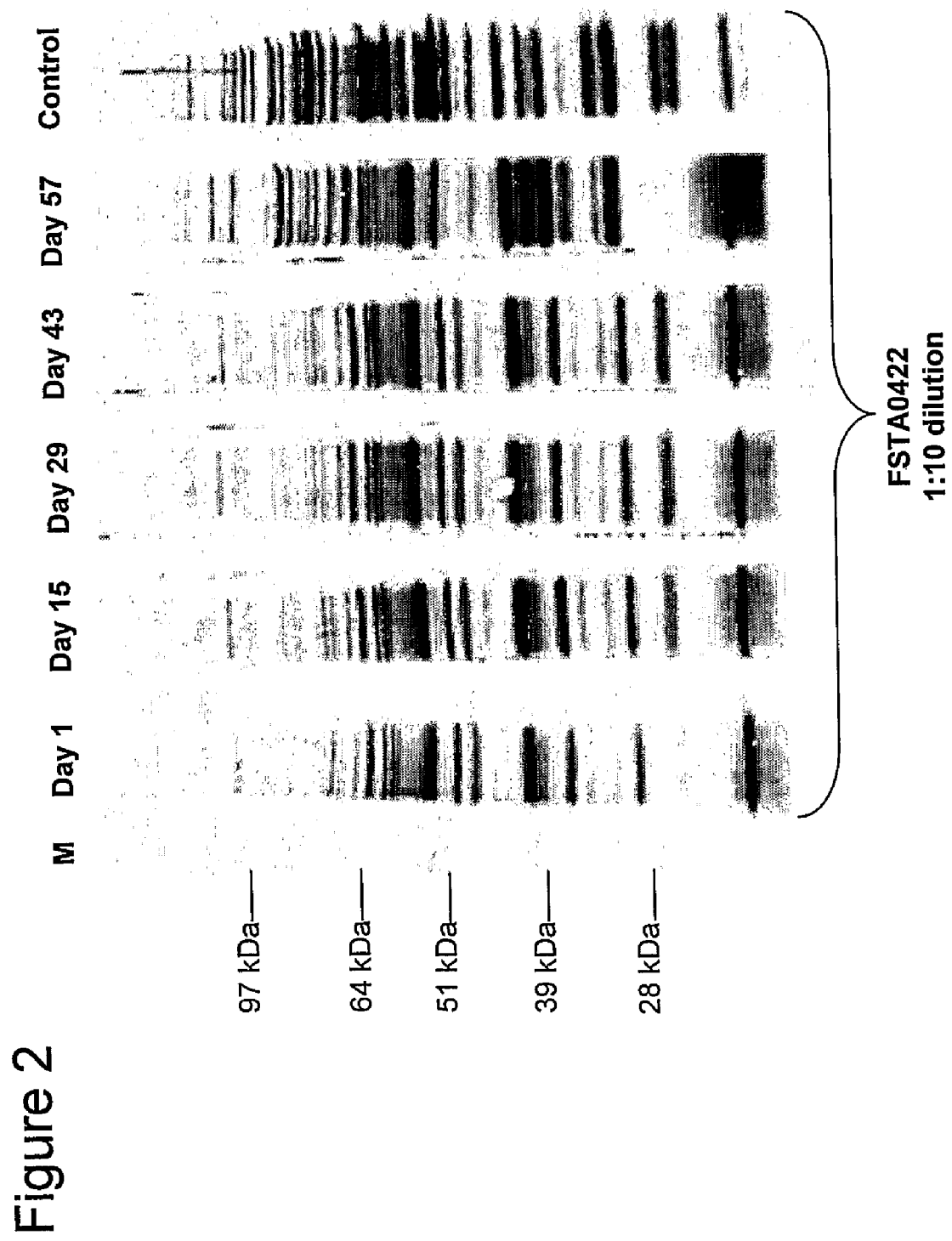
FIG. 2 illustrates the immune response of subject given 0.15 mg dose on western blotting. Day 1—before vaccination; day 15—after one vaccination; day 29—after two vaccinations; day 43—after three vaccinations; and day 57—after four vaccinations.
Figure 3:
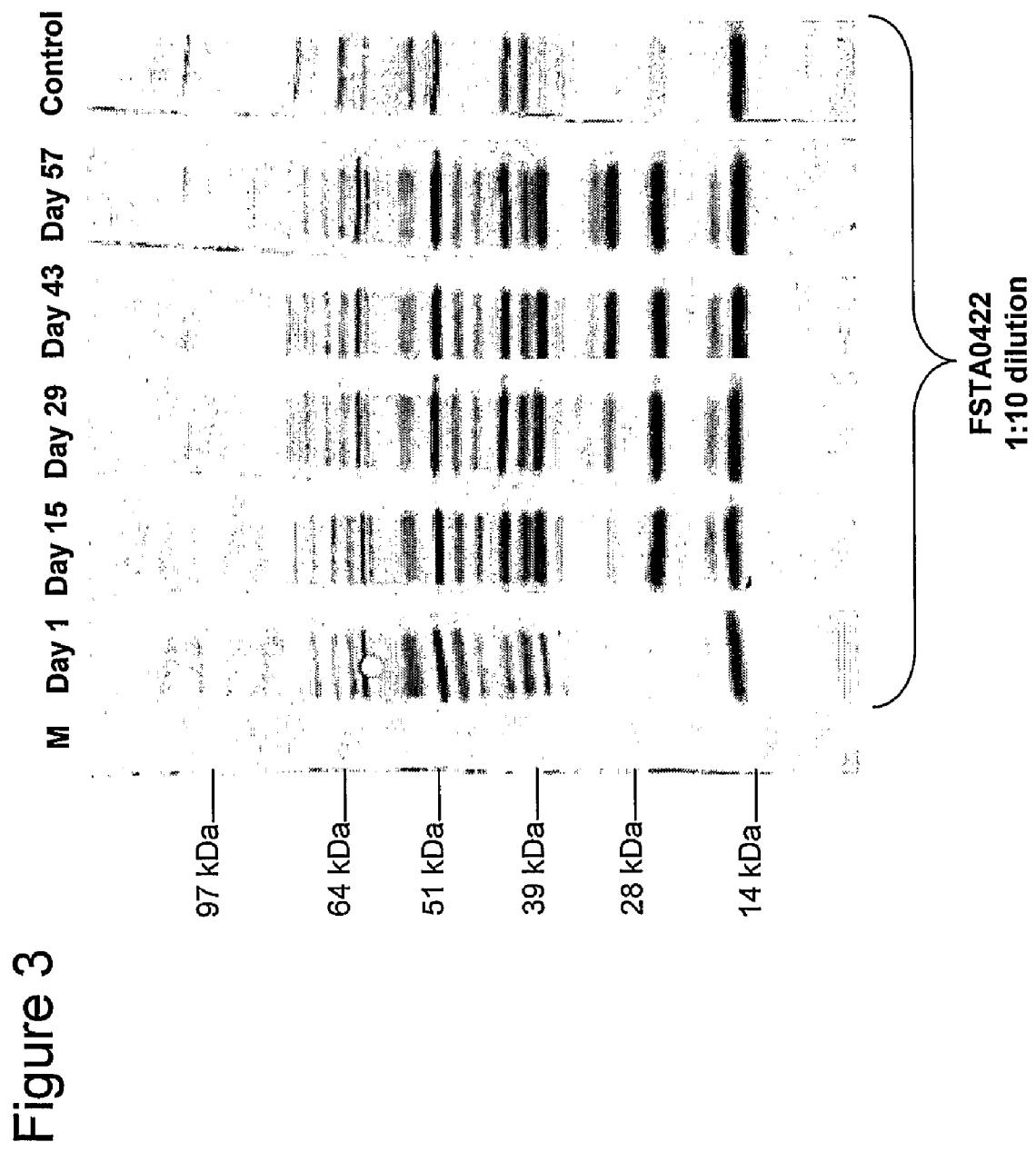
FIG. 3 illustrates the immune response of subject given 0.36 mg vaccine on western blotting Day 1—before vaccination; day 15—after one vaccination; day 29—after two vaccinations; day 43—after three vaccinations; and day 57—after four vaccination
Figure 4:
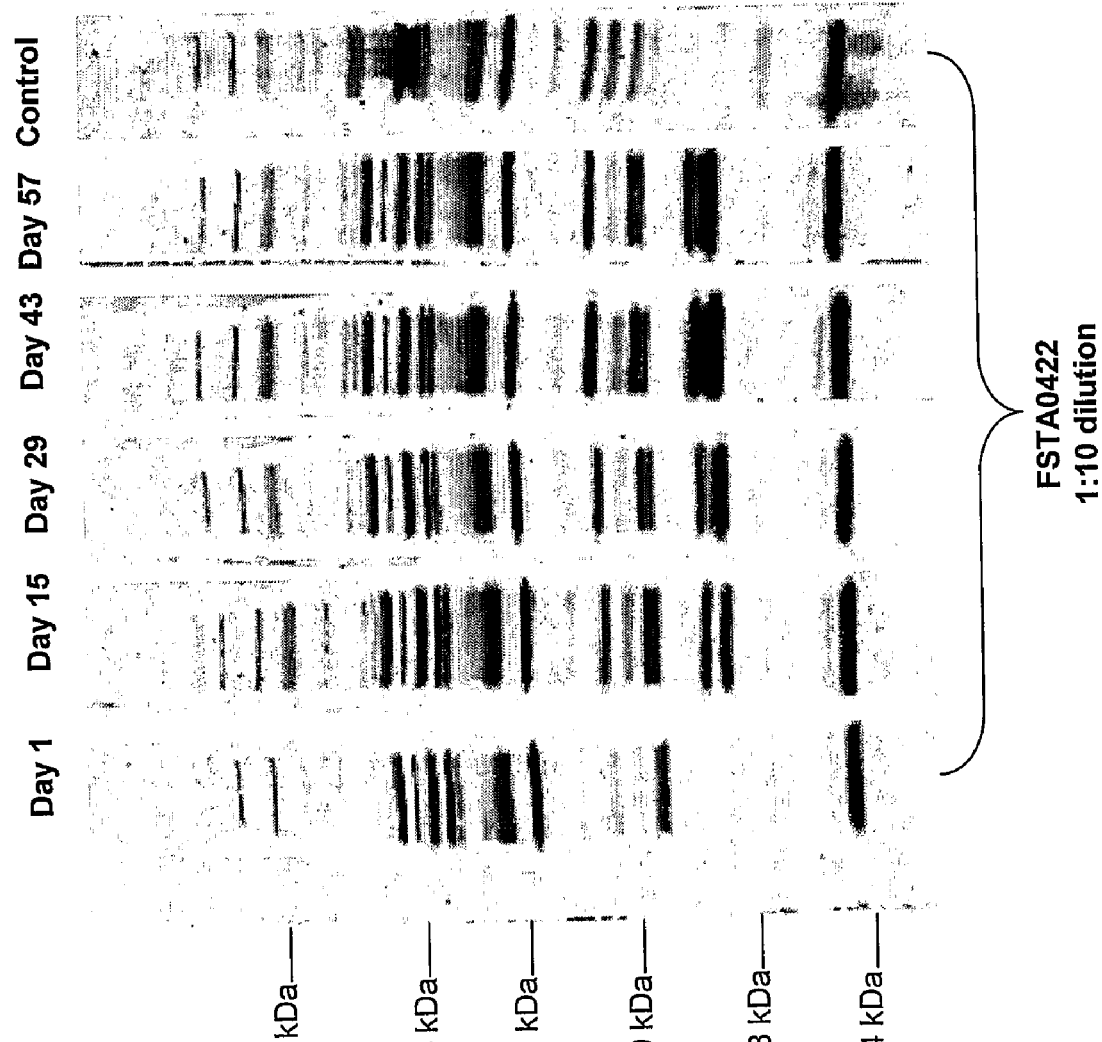
FIG. 4 illustrates the immune response of subjects given 0.45 mg vaccine on western blotting. Day 1—before vaccination; day 15—after one vaccination; day 29—after two vaccinations; day 43—after three vaccinations; and day 57—after four vaccinations.

The bacteria are cultured in tryptone soya both and mixed with 10% glycerol, aliquoted and stored as Master Seed Bank and Working Seed Bank at −70° C. in liquid form and at +4° C. following freeze-drying. Bacteria were prepared by plating out bacteria from one vial of Working Seed Bank and growing on tryptone soya agar plates for 16 hours at 37° C. The bacterial growth is then harvested into a small volume of tryptone soya broth which is in turn used to inoculate bigger volumes of tryptone soya broth. The liquid culture is incubated with agitation for 16 hours at 37° C. The bacteria are then concentrated by centrifugation. The concentration is adjusted with tryptone soya broth and the culture shaken with chloroform in a 5:3 culture to chloroform ratio and left to stand for 15-20 minutes at 20° C. to allow phase separation. The bacterial suspension is top collected, centrifuged at 3-4000 rpm for 15 minutes and the pellet resuspended in sterile distilled water or phosphate buffered saline. This is centrifuged again and the pellet resuspended as above.

Alternatively, a staphylococcal strain was isolated in vegetable peptone agar and subcultured three times in vegetable peptone agar. A liquid culture of bacteria was grown for 16 hours at 37° C. in vegetable peptone broth and shaken with chloroform and left to stand for 15-20 minutes at 20° C. to allow phase separation. The bacterial suspension is top collected, centrifuged and the pellet resuspended in water or phosphate buffered saline, centrifuged and resuspended as above.

Optionally staphylococcal preparations inactivated with chloroform and washed and resuspended in the relevant medium are immediately frozen and freeze dried for storage.

EXAMPLES

The vaccine and placebo phosphate buffered saline (PBS) were prepared under Good Manufacturing Practice (GMP) by the Norwegian Institute of Public Health in Oslo, Norway and the double blind placebo controlled Phase I clinical trial was carried out by Simbec Research Limited, Merthyr Tydfil, UK. Testing of sera from volunteers was carried out under GLP and in house at VRI laboratories and by Professor Jan-Ingmar Flock, Karolinska Institute, Stockholm, Sweden.

Forty eight male volunteers between the ages of 18 and 55 were divided into 3 groups receiving subcutaneous doses of vaccine SA75 containing 0.15 mg, 0.36 mg, or 0.45 mg of protein. In each group 12 volunteers received vaccine and 4 received a corresponding placebo phosphate buffered saline (PBS). A total of four inoculations were administered at 2 week intervals. Volunteers remained in the clinical trial unit for 8 hours post dosing and were monitored for local (erythema, induration, swelling, haemorrhage, warmth, burning, pruritis and pain) and systemic reactions (malaise, fatigue, flu-like symptoms, feeling of hot/cold, vomiting and headaches) on the day of dosing and on Days 2, 3, and 8 post dosing. Blood pressure, ECG, temperature, urinalysis, haematological and biochemical tests were also carried out. Blood samples for the purpose of evaluating immune response were taken before the first vaccination and two weeks after each of four subsequent vaccinations.

Sera from volunteers before and after vaccination were tested against whole chloroform-inactivated homologous organism by ELISA and western blotting to evaluate immune response to the whole organism. Sera were also tested by ELISA for the presence of antibodies to collagen binding protein, fibrinogen binding protein, fibronectin binding protein and extracellular adherence protein (Professor Jan-Ingmar Flock).

As expected with a whole cell vaccine, transient local reactions were observed at the site of injection in vaccinated subjects. There was a clear dose related response and the 0.15 mg and 0.36 mg doses demonstrated acceptable mild to moderate levels of local reaction. A dose of 0.45 mg was considered the maximum tolerated dose based upon the more pronounced local reaction. One subject in the 0.45 mg dose group had a severe local reaction which led to their withdrawal from the study (Table 1).

There were no significant systemic adverse effects attributable to the vaccine at doses of 0.15 mg and 0.36 mg protein. At the higher dose of 0.45 mg there was an increased incidence of pyrexia with a mild increase in temperature reported in 4 subjects. Three subjects receiving the 0.45 mg dose experienced general malaise with two classified as mild and one as severe. No pyrexia or malaise was observed in the placebo, 0.15 and 0.36 mg groups. Mild to moderate pain in the extremities was reported in the 0.45 mg dose group on a number of occasions during the course of the study. Severe pain was only reported on a single occasion. Headache which was always mild to moderate was reported in all groups including the placebo group and increased with increase in dose level (Table 2).

All adverse events were reported over a period of a few hours to several days following vaccination and were all transient lasting anything from a few hours to a few days.

On western blotting 75% of the vaccinated subjects demonstrated strong reactivity compared to none of the placebo subjects (p<0.0001) where strong reactivity was taken as five or more incidents of increase in polypeptide reactivity in terms of intensity or number in post compared to pre-vaccination sera. Weak reactivity was taken as less than four increases in polypeptide reactivity in terms of intensity or number in post compared to pre-vaccination sera; Table 3 and FIGS. 1, 2, 3, 4.

Figure 5:
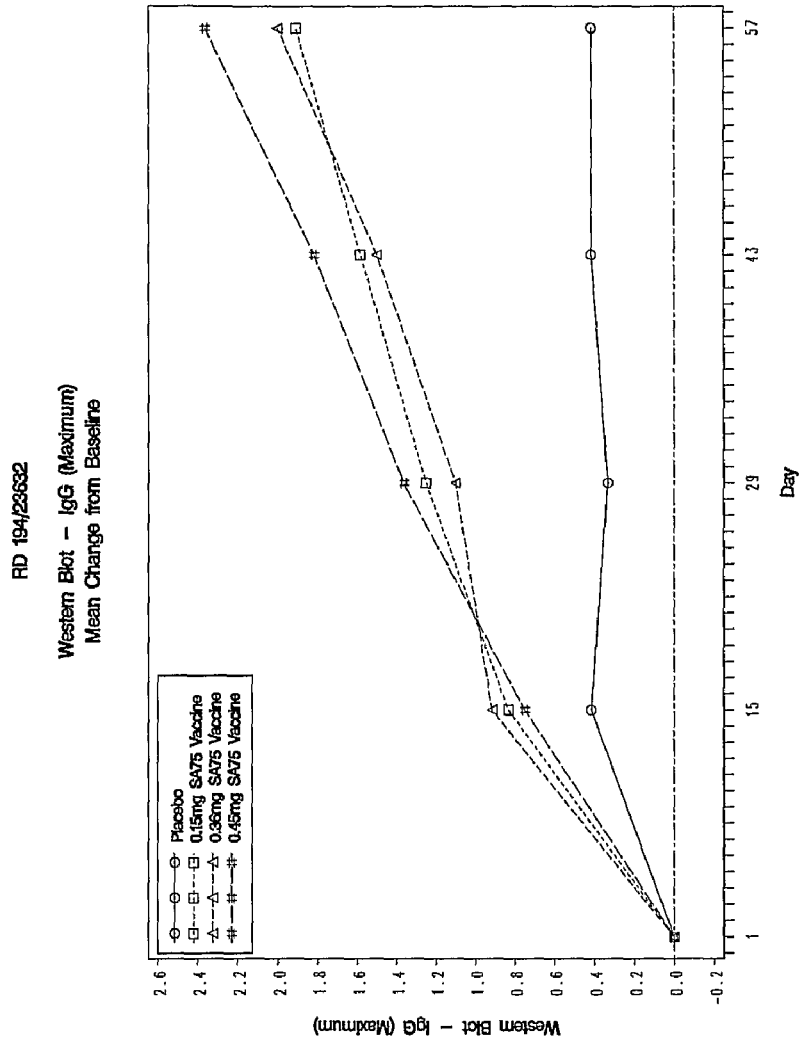
FIG. 5 illustrates the mean change from base line on western blotting of sera before and after vaccination for vaccinated and placebo subjects. Day 1—before vaccination; day 15—after one vaccination; day 29—after two vaccinations; day 43 after three vaccinations; and day 57—after four vaccinations.

The response was dose related and there was a clear relationship between the immune reactivity of sera and number of vaccinations; FIG. 5.

Figure 6:
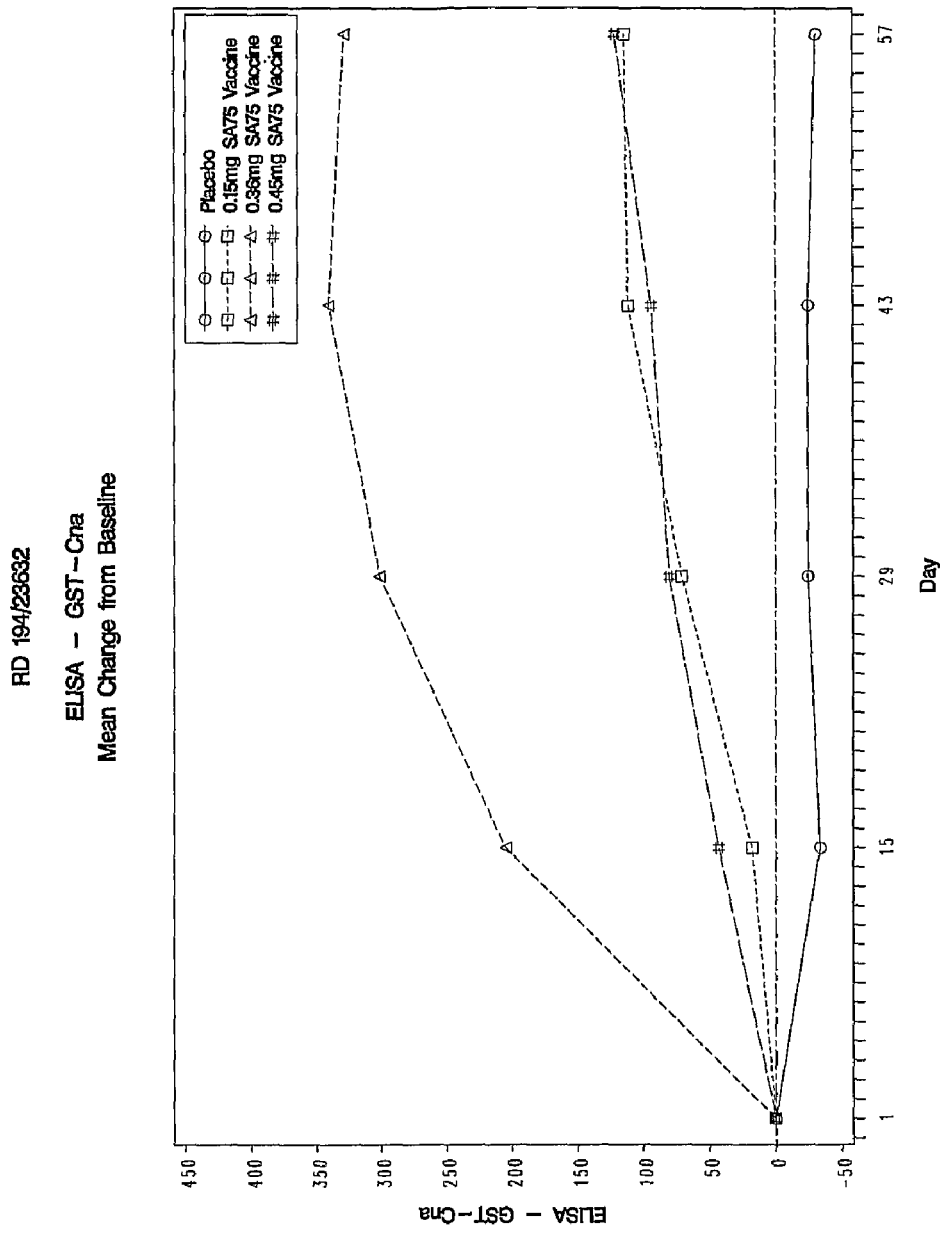
FIG. 6 illustrates the mean change from baseline against collagen binding protein of sera before and after vaccination for vaccinated and placebo subjects.

Antibody levels against collagen binding protein were significantly increased in vaccinated volunteers (p0.005) with the number of responders increasing with the number of vaccinations; Table 4 and FIG. 6. There was no significant increase in antibodies to the other binding proteins tested.

The chloroform-inactivated *S. aureus* vaccine designated SA75 was shown to be safe when tested in formal toxicology tests in rabbits and produced an immune response demonstrated using ELISA and western blotting in rabbits. This and other additional data then allowed use of the vaccine in a double blind placebo controlled trial in human volunteers. The SA75 vaccine was shown to be safe and produced an immune response in male volunteers.

There were no clinically significant changes in vital signs, ECG parameters or laboratory safety tests observed during the clinical trial. In general there was no difference in systemic response in relation to the number of vaccinations or dose given.

There was a clear relationship of local reactivity to vaccine dose level reported, with no discernable difference in local reactions between the different vaccinations at any dose level. There was also a relationship between vaccination dose and the frequency and extent of erythematous reaction but this was not related to the number of vaccinations given. The 0.15 mg and 0.36 mg doses were considered acceptable on safety grounds.

The immune response measured by ELISA and western blotting demonstrated a clear difference between the frequency of immune response in vaccinated subjects compared to those who received placebo.

Cross Reactivity

Figure 7:
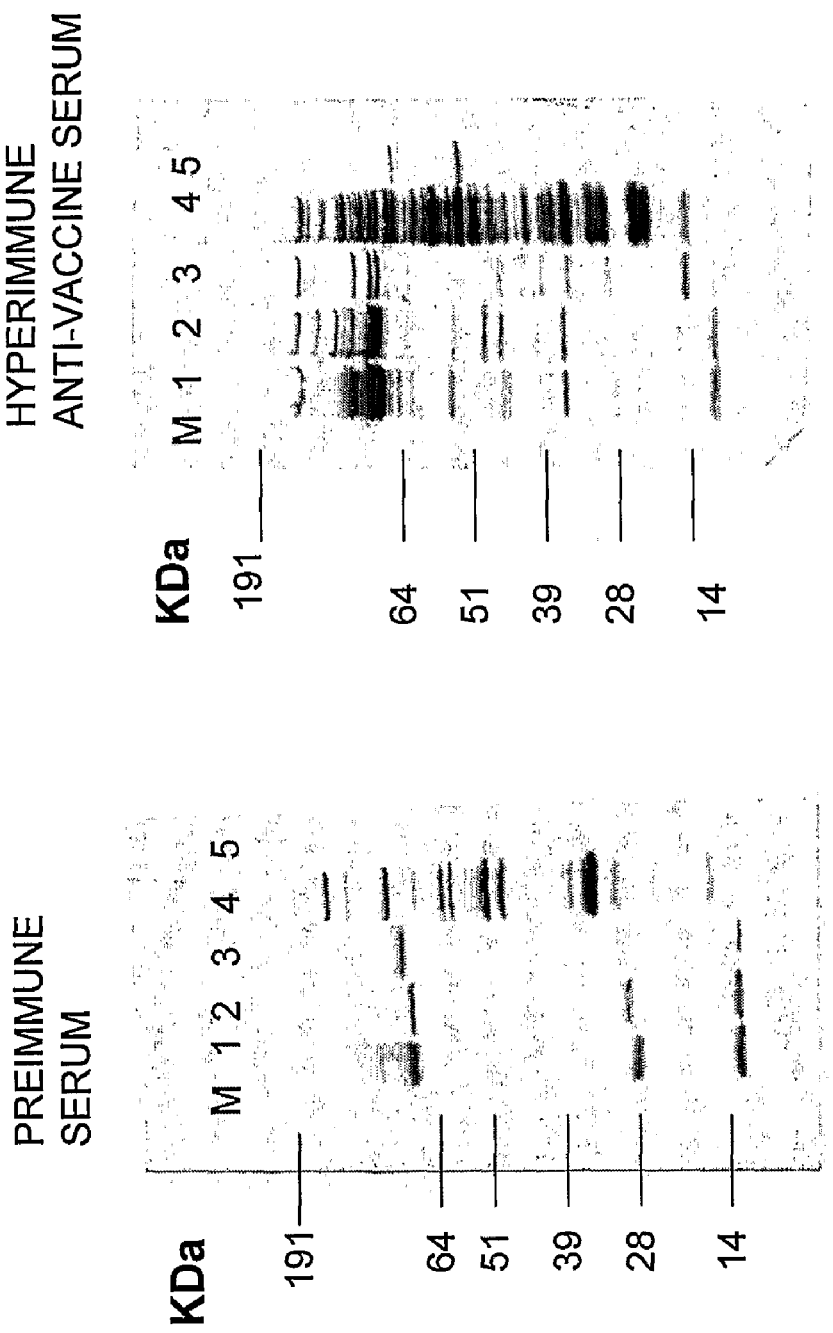
FIG. 7 illustrates the cross reactivity of anti-sera produced by vaccination of rabbits against a number of unrelated bacteria; M: Molecular weight marker; track 1 *E. coli*; track 2 *Klebsiella edwardii*; track 3 *Proteus mirabilis*; track 4 *S. aureus* P/DFO 75; track 5 *Candida albicans*; preimmune and hyperimmune serum after 4 inoculations of the *S. aureus* P/DFO 75 vaccine into a rabbit were used.

FIG. 7 illustrates an immunoblot and represents the activity of a rabbit prior to vaccination with the Staphylococcal vaccine (labelled Rabbit 19 PI) and following 4 vaccinations (labelled Rabbit 19 after 4 vaccinations).

Opsonic Antibodies

Figure 8:
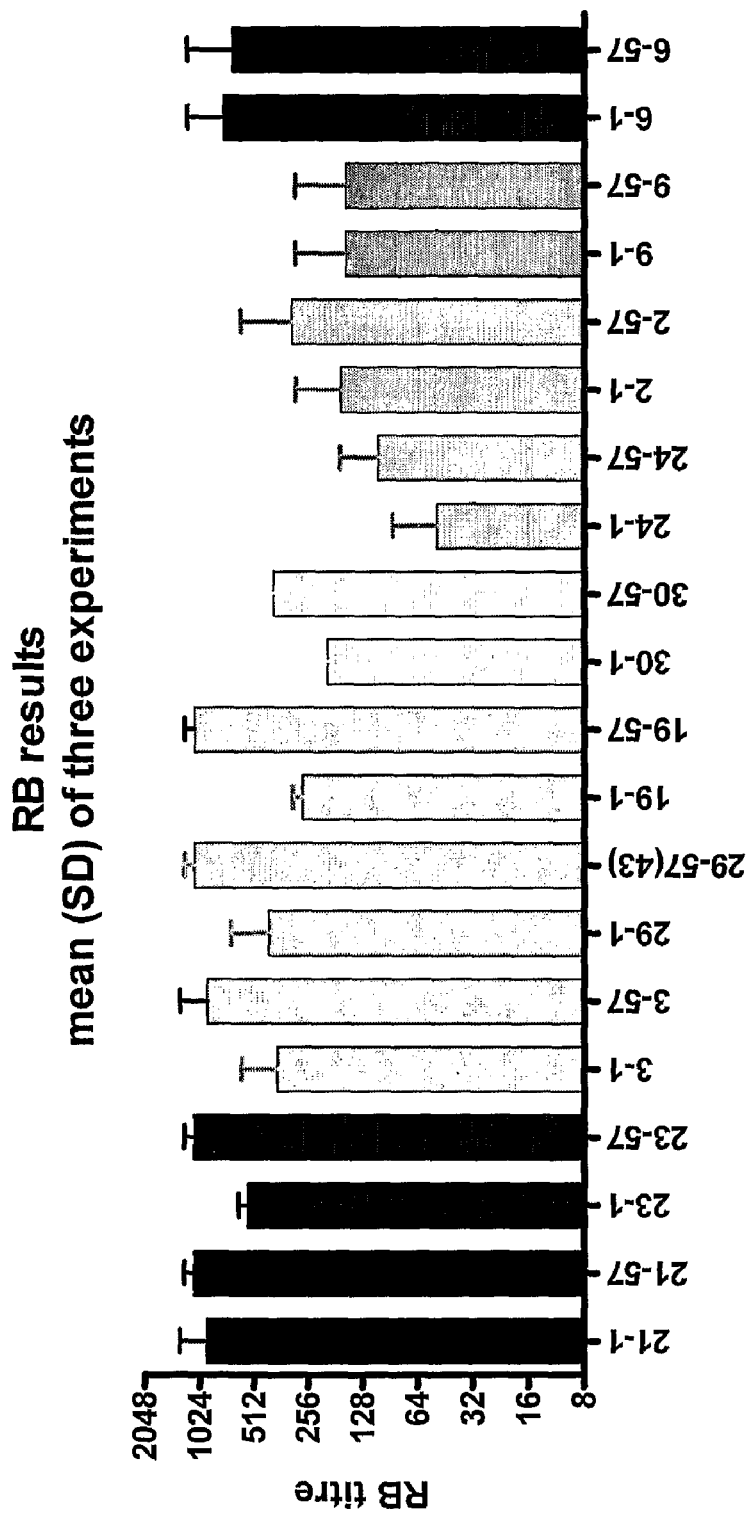
FIG. 8 illustrates the production of opsonic antibodies after vaccination; Subjects 2, 6, 9, and 21 are placebo Day 1 sample is before vaccination and Day 57 is after 4 vaccinations. Subjects 19, 23, 24, 29, 30 are subjects given 0.45 mg vaccine. Subject 3 was given 0.15 mg vaccine.

FIG. 8 demonstrates the opsonic antibody response in six patients who received vaccination and four patients who received placebo vaccination. There is increase in opsonic antibody level in the vaccinated patients but in only one to any significant extent namely patient 2 (placebo). It is of course perfectly possible that this patient had an intercurrent Staphylococcal infection which would explain this result.

As anticipated there was a highly significant immune response against the homologous Staphylococcal strain used to prepare the vaccine in the penultimate column to the right. There were new immunoreactive bands in the vaccinated serum against *E. coli, Klebsiella* and *Proteus* which are pathogens responsible for a wide variety of human infections including wound infections and thus there is a reasonable prospect that the vaccine will provide protection against not only Staphylococcal wound infection but other infections caused by these three and probably other if not all pathogenic microorganisms. It is also of interest that the vaccinated serum has developed antibodies against *Candida albicans*—a frequent cause of yeast infections particularly in female subjects—which is of great interest in as much as *Candida albicans* is a eukaryotic organism while Staphylococci and the other organisms tested are prokaryotic organisms. The last observation adds weight to the feasibility of a Universal vaccine based on our preparative method.

Longevity

Table 5 illustrates that the immune response as adjudged by immunoblotting which we thought was the most useful indicator of immune response maintains irrespective of vaccine dose for three to six months following vaccination. The table does not illustrate an important aspect that there was an insignificant decline in immune response at 3 and 6 months and clearly no subject had returned to the pre vaccination status by that time. The protocol of the trial regrettably did not allow estimation of antibody levels beyond six months which was perhaps an error in the formulation of our study.

Subjects who received placebo vaccination and who of course had a base line level of antibody reactivity against Staphylococcal antigens which obtains in every subject remained unchanged in three to six months indicating an interesting lack of variability in human subjects in general and adds weight to the unequivocal increase in immune reactivity in vaccinated subjects.

The invention claimed is:

1. A composition comprising an inactivated staphylococcal cell wherein said cell:
    i) is a gram positive cocci;
    ii) expresses at least the enzyme catalase;
    iii) induces an immune response that produces antibodies that bind at least staphylococcal collagen-binding protein; and
    iv) is resistant to the antibiotic penicillin,
    wherein said staphylococcal cell is *Staphylococcus aureus* deposited as National Collection of Type Cultures (NCTC) accession number 13408.

2. The composition according to claim 1, wherein said staphylococcal cell induces an immune response that produces antibodies that bind collagen binding protein.

3. The composition according to claim 1, comprising said staphylococcal cell at a protein concentration of not more than about 1.0 mg or 0.45 mg bacterial protein/ml.

4. The composition according to claim 1, comprising said staphylococcal cell at a protein concentration of at least 0.0001 mg or 0.1 mg bacterial protein/ml.

5. The composition according to claim 1, comprising said staphylococcal cell at a protein concentration of between 0.0001-1 mg bacterial protein/ml.

6. The composition according to claim 1, comprising said staphylococcal cell at a protein concentration of between 0.1-0.45 mg bacterial protein/ml.

7. The composition according to claim 1, comprising said staphylococcal cell at between 0.25-0.36 mg bacterial protein/ml.

8. The composition according to claim 1, comprising said staphylococcal cell at about 0.35 mg bacterial protein/ml.

9. The composition according to claim 1, wherein said composition comprises an adjuvant and/or excipient.

10. The composition according to claim 1 further comprising at least one additional anti-bacterial agent.

11. The composition according to claim 10, wherein said anti-bacterial agent is a different vaccine and/or immunogenic agent.

12. The composition according to claim 1, formulated for administration as a nasal spray.

13. The composition according to claim 12, provided in an inhaler for delivery of an aerosol.

14. A *Staphylococcus aureus* cell as deposited under National Collection of Type Cultures (NCTC) accession number 13408.

15. A bacterial cell culture comprising a *Staphylococcus aureus* cell as deposited under National Collection of Type Cultures (NCTC) accession number 13408.

16. A method of producing an immune response to *Staphylococcus aureus* in a subject, comprising,
    comprising administering to the subject an effective amount of the composition of claim 1, thereby inducing the immune response to *Staphylococcus aureus* in the subject.

17. The method of claim 16, wherein the subject is human.

* * * * *